United States Patent [19]

Dolan et al.

[11] Patent Number: 5,566,872
[45] Date of Patent: Oct. 22, 1996

[54] VIAL FLOSS DISPENSER

[75] Inventors: John W. Dolan, Boothwyn, Pa.; John W. Spener, Jr., Rising Sun; Rickey I. Hill, Elkton, both of Md.

[73] Assignee: W. L. Gore & Associates, Inc., Newark, Del.

[21] Appl. No.: 272,163

[22] Filed: Jul. 8, 1994

[51] Int. Cl.$^6$ .................................................. A61C 15/04
[52] U.S. Cl. ........................... 225/41; 225/45; 225/47; 225/90; 242/137.1; 242/588.6; 242/598.6; 242/597.3; 132/325
[58] Field of Search ................................. 225/39, 40, 41, 225/44, 45, 46, 53, 77, 80, 90, 47; 132/324, 325; 242/138, 137.1, 588.6, 596.7, 598.3, 598.6, 599.3, 599.4, 606; 112/231, 232; D28/64

[56] References Cited

U.S. PATENT DOCUMENTS

| | | | |
|---|---|---|---|
| 127,982 | 6/1872 | Merrick | 242/138 |
| D. 271,431 | 11/1983 | Seelig | D28/64 |
| D. 339,215 | 9/1993 | Spencer, Jr. | D28/64 |
| D. 339,426 | 9/1993 | Spencer, Jr. | D28/64 |
| 817,050 | 4/1906 | De La Cour | 242/138 |
| 1,038,249 | 9/1912 | West | 242/138 |
| 2,340,184 | 1/1944 | Gray | 225/41 X |
| 2,929,541 | 3/1960 | Castelli et al. | 225/44 |
| 3,246,815 | 4/1966 | Aronson | 225/44 |
| 3,319,854 | 5/1967 | Palmer | 225/47 X |
| 3,480,190 | 11/1969 | Freedman | 225/33 |
| 4,111,089 | 9/1978 | Montaruli | 225/45 X |
| 4,162,688 | 7/1979 | Tarrson et al. | 132/322 |
| 4,934,389 | 6/1990 | Pettiford | 132/325 |
| 5,076,302 | 12/1991 | Chari | 132/325 |
| 5,156,311 | 10/1992 | Spencer, Jr. et al. | 225/41 |

FOREIGN PATENT DOCUMENTS 9113594  9/1991  WIPO.

OTHER PUBLICATIONS

Literature: Glide™ Floss Specification: Vial Product; W. L. Gore and Associates, Inc.; 1993.

Primary Examiner—Rinaldi Rada
Assistant Examiner—Clark F. Dexter
Attorney, Agent, or Firm—Victor M. Genco, Jr.; David J. Johns

[57] ABSTRACT

The present invention is an improved vial-type floss dispenser. The floss dispenser has a spool of floss mounted upright in a cylindrical container with a unique cap design that allows floss to be smoothly dispensed through the cap of the dispenser, essentially parallel to the axis of the spool of floss. Tangling and snagging problems previously encountered with top-dispense floss vials of this type are avoided by the improved cap design that allows the free spinning of the spool within the container. The top-dispense mechanism of the present invention enables the use of a number of other improved features, including a protective lid that fully covers an exposed leader of floss between uses.

8 Claims, 3 Drawing Sheets

VIAL FLOSS DISPENSER

BACKGROUND OF THE INVENTION

1. Field of the Invention

The present invention relates to containers for holding and dispensing floss material, and particularly vial-shaped floss dispensers.

2. Description of Related Art

Floss is dispensed from a wide variety of containers and dispensers. Most common floss dispensers are a rectangular package with a sideways mounted circular spool of floss material dispensing floss through a hole in the top of the package past a cutting blade. The top of the package and the cutting blade are generally protected by a hinged lid. A particular successful example of this basic design in taught in U.S. Pat. Nos. 5,156,311, and D-339,426, which includes a view-window through which the amount of floss in the container can be monitored. Since floss is dispensed from these containers in a direction perpendicular to the axis of the floss spool, floss generally dispenses very smoothly.

One problem with this basic design is limited holding capacity of the container. While such packages can readily hold 50 to 75 yards of floss fiber, significant increase in the amount of floss above this volume requires a redesign of the container. When W. L. Gore & Associates, Inc., Flagstaff, Ariz., introduced a floss package holding 200 yards of material, it opted for a cylindrical vial, with floss mounted on an upright mounted spool loosely inserted within the cylindrical container. While it would be preferred to dispense the floss from the top of such a container (i.e., in a direction approximately parallel to the axis of the spool), it was discovered that the floss would not cleanly payoff the spool when the floss was fed through a hole in the top of the vial, becoming periodically tangled and jammed during pay-off.

To solve this pay-off problem, a hole was introduced in the side of the floss vial through which the floss was threaded. To dispense, floss is pulled out perpendicular to the axis of the spool and then cut on a blade mounted on the top of the vial. This design provides very smooth floss pay-off. Unfortunately, when floss is threaded in this manner, a length of floss is left exposed on the outside of the vial between the hole in the vial and the top-mounted cutting blade. Further, the inability to seal this exposed length of floss makes it less desirable to provide a re-sealable lid on the top of the vial to protect the cutting blade and the exposed floss. Improvement in this design, particularly in the ability to completely seal the floss before sale and between uses, is thus desirable.

Accordingly, it is a primary purpose of the present invention to provide a floss dispenser with the large capacity of a vial but with ready pay-off of the floss material.

It is another purpose of the present invention to provide a vial-type floss dispenser that can dispense floss through one of its ends without tangling or jamming.

It is still another purpose of the present invention to provide a vial-type floss dispenser that can dispense floss through one of its ends so that the end, as well as the exposed floss and the cutting blade, can be protected with a removable lid between uses.

These and other purposes of the present invention will become evident from review of the following specification.

SUMMARY OF THE INVENTION

The present invention is an improved floss dispenser package for holding and dispensing floss. The preferred floss dispenser of the present invention comprises an upright spool of floss material packaged within cylindrical container. Unlike previous vial-type floss dispensers, the spool of floss in the present invention is centered within the dispenser by mating its with a unique cap on the end of the container. This cap includes a recess in its center into which a projection from the spool seats while remaining free to spin around its axis. An annular groove around the recess in the cap allows floss to spin off the spool and through an opening in the cap. When constructed in this manner, the floss dispenser provides very smooth and reliable floss delivery through its cap without the jamming and tangling problems previously experienced with top-dispense upright floss dispensers.

The reliable top floss dispensing of the vial floss dispenser of the present invention provides a number of distinct advantages over previous dispensers of this type. For instance, the cap of the present invention includes a lid that completely covers the top of the cap and protects exposed floss and a cutting blade contained in the cap. In this manner risk of contamination or accidental injury is vastly reduced. Another improved feature of the cap is a contoured shape that makes the floss more easily grasped by a user.

DESCRIPTION OF THE DRAWINGS

The operation of the present invention should become apparent from the following description when considered in conjunction with the accompanying drawings, in which.

DETAILED DESCRIPTION OF THE INVENTION

The present invention is an improved dispenser for storing and distributing floss.

Figure 1:
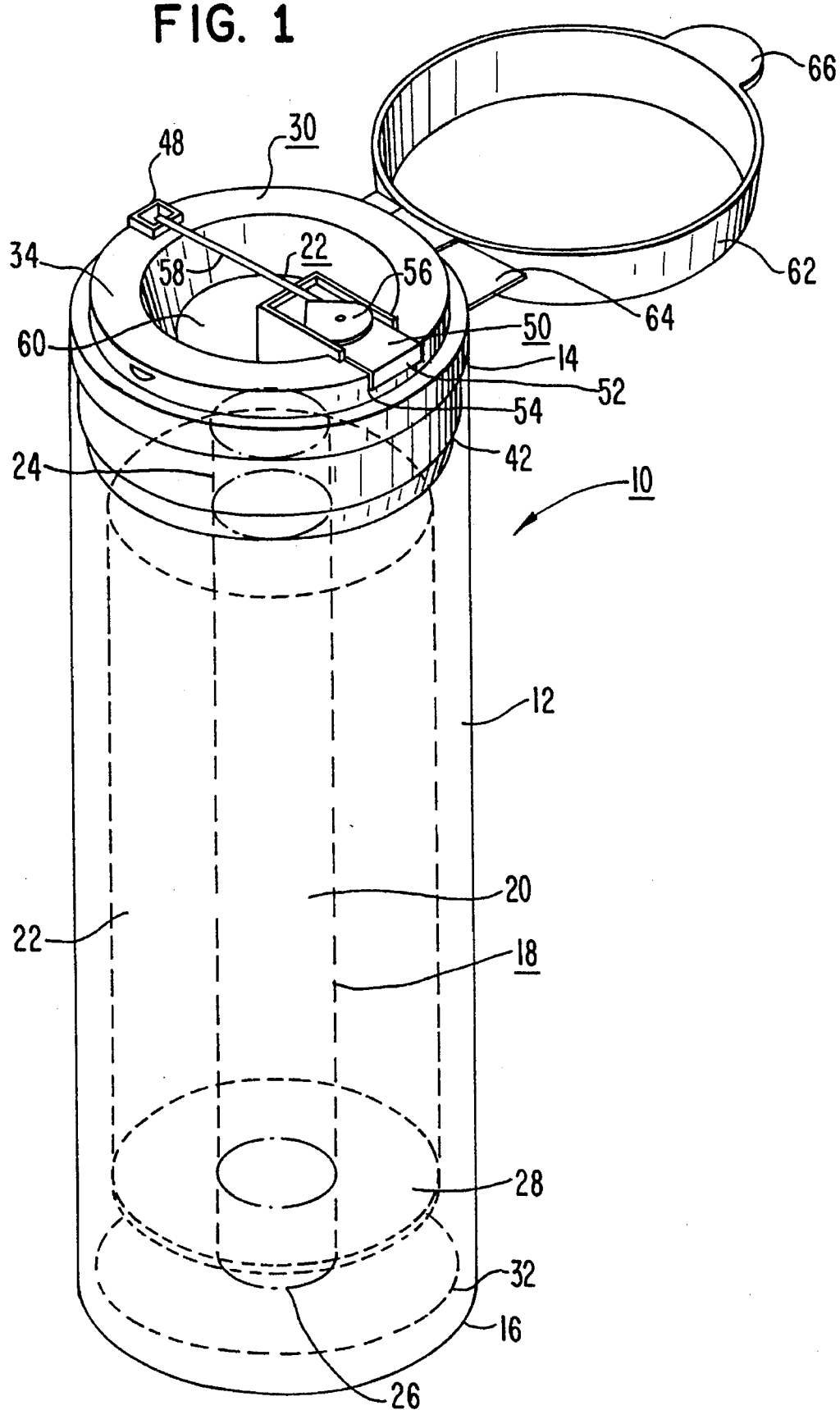
FIG. 1 is a three-quarter isometric view of a vial floss dispenser of the present invention, with its lid shown in an open orientation and with a spool of floss within the dispenser shown in phantom.
Figure 2:
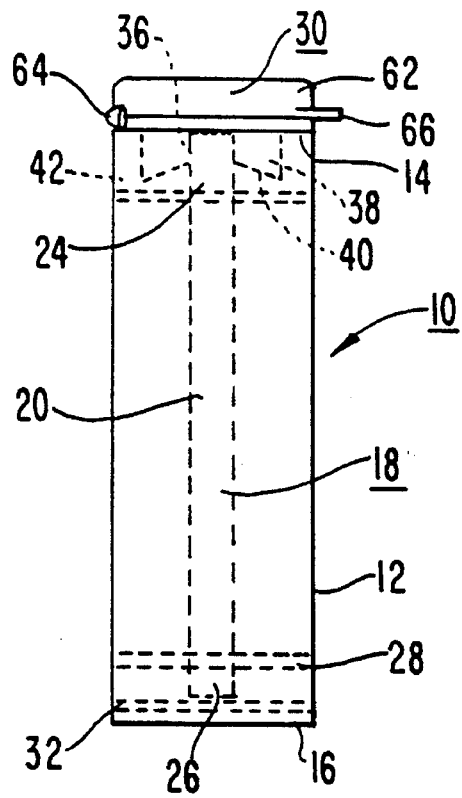
FIG. 2 is a side elevation view of a floss container of the present invention, with the interior of the floss dispenser shown in phantom and with its lid shown in a closed orientation.

As is shown in FIGS. 1 and 2, the dispenser 10 of the present invention comprises a cylindrical vial container or vial case 12 having a first open end 14 and a second closed end 16. Inserted within the container 12 is a spool 18 having a hub 20 around which is wrapped a length of floss 22. The spool 18 is mounted with its axial hub 20 parallel to the longitudinal length of the container 12. The hub extends beyond the floss on either end, forming projections 24, 26. The spool 18 includes a circular disc 28 attached to its lower end. The disc 28 is proportioned to fit within the container 12 so as to assist in keeping the lower end of the spool centered within the container 12 while allowing the spool to freely turn. Additionally, the disc 28 also serves to assist in retaining the floss on the spool while keeping the floss away from projection 26.

The open end 14 of the dispenser 10 is sealed with a cap 30. Preferably, the cap 30 is removable so as to provide access to the interior of the dispenser 10. The closed end 16 of the dispenser 10 may be simply constructed in a sealed manner or may include a permanent or removable end plug 32. It is particularly preferable that the end plug 32 and the circular disc 28 both be formed from a transparent material, such as plastic or glass, so that the floss wrapped around the spool can be seen through the bottom of the dispenser 10. This provides an easy method for a user to determine the amount of floss left within the dispenser.

As has been explained, a vial floss dispenser design is believed to be particularly effective at holding a large quantity of floss in a highly serviceable manner. Unfortunately, previously this construction has not provided easy floss pay-out from the spool where attempts have been made to dispense floss through its cap 30 (i.e., in a direction parallel to the axis of the spool). This method of dispensing tends to lead to tangling and snagging of the floss within the container during pay-out. The present method of correcting this problem has been to feed the floss out of a hole in the side of the container, perpendicular to the axis of the floss spool, and then running the floss up the outside of the container to a cutting blade in the dispenser's cap. This method of distribution is far from satisfactory since a segment of floss is then left exposed on the side of the container and the top of the container (along with its exposed cutting blade) cannot be readily covered without snapping a lid over the exposed segment of floss. These constraints have been corrected in the present invention through the development of the design of improved cap 30.

Figure 3:
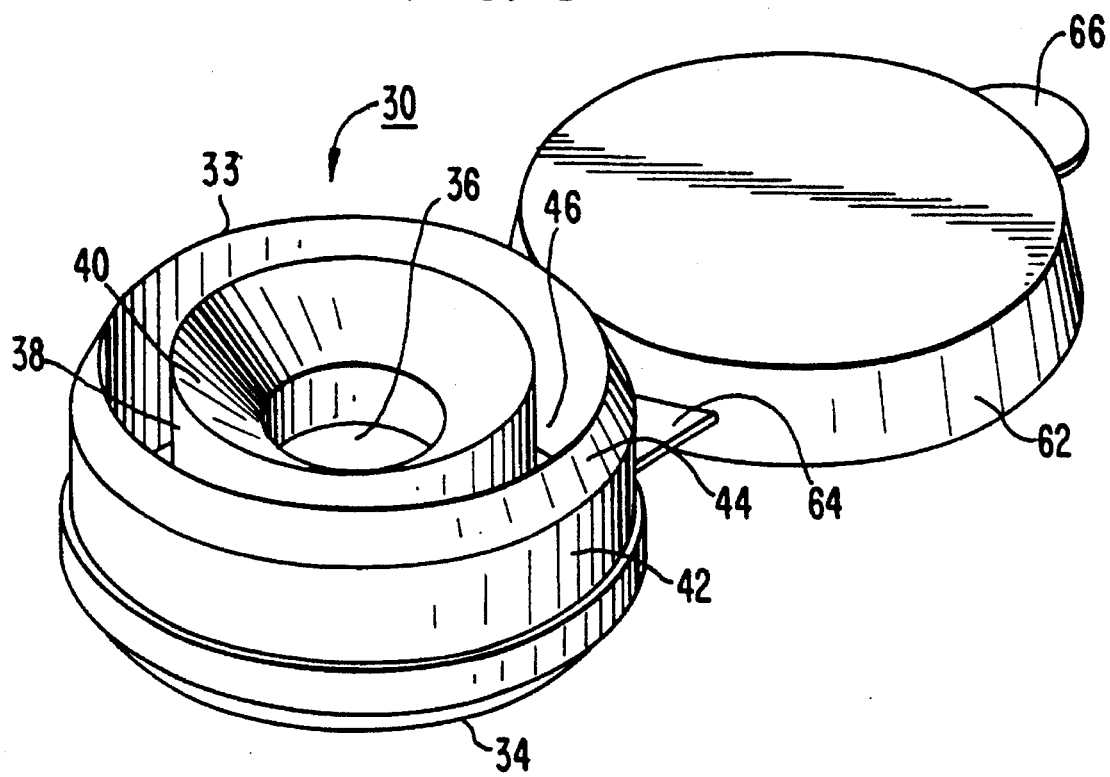
FIG. 3 is a three-quarter isometric view of the bottom of a cap of a floss dispenser of the present invention.

The cap 30 of the present invention has a bottom surface 33 and a top surface 34, each incorporating unique features. The bottom surface 33 of the cap is best illustrated in FIG. 3. The bottom of the cap 30 has a recess 36 therein defined within a circular lip 38. Preferably, the lip 38 includes an inward taper 40, inclined toward the recess 36 in the manner illustrated. As is shown in FIG. 2, the recess 36 is adapted to receive projection 24 of the hub 20 when the cap 30 is mounted on the container 12. The recess 36 is proportioned to provide a close yet unrestrained retention of the projection 24 in such a manner that the spool of floss will spin freely within the cap 30 as floss is dispensed from the spool. The taper 40 assists in centering the hub 20 into the recess 36 when the cap 30 is mounted on the container 12.

The cap 30 has an outside wall 42 that is proportioned to fit snugly within the open end 14 of container 12 to retain the cap 30 within the container 12. Preferably, the outside wall 42 is tapered inwardly on its end 44 to assist in fitting the cap 30 within the container 12.

An annular groove 46 is defined between the circular lip 38 and the outside wall 42 in cap 30. This groove 46 provides sufficient space to allow floss dispensing from the spool to pass freely upwardly through an opening 48 in the cap 30, such as that shown in FIGS. 1 and 4.

It has been determined that floss will dispense very readily through the opening 48 in cap 30 when the spool is retained in the manner described above. The use of recess 36 to retain the floss spool 18 in a centered orientation, with floss dispensing off the spool 18 and upwardly through annular groove 46 and into opening 48, avoids the jamming problems previously encountered with top dispense vial floss dispensers where the floss spool was not maintained in a consistent, centered spinning orientation. As a result, the floss dispenser of the present invention provides smooth, unencumbered floss pay-out through one or more openings placed in its cap.

Figure 4:
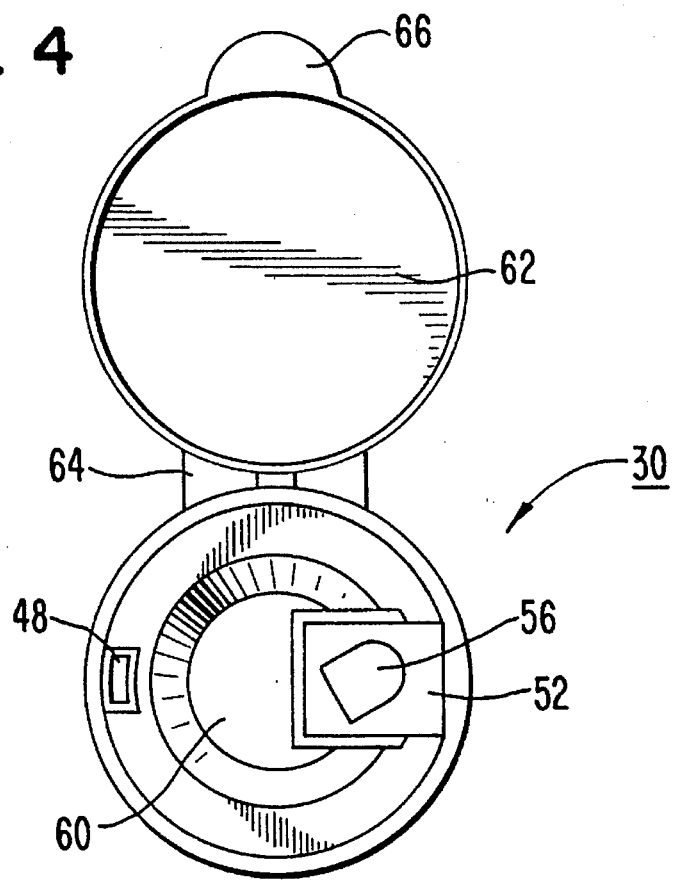
FIG. 4 is a top plan view of a cap of the floss dispenser of the present invention, with a hinged lid shown in an open orientation.
Figure 5:
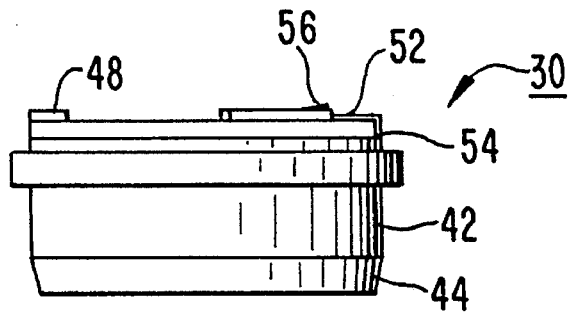
FIG. 5 is a side elevation view of a cap of the floss dispenser of the present invention, shown without an attached lid.

The advantages of a vial floss container with top pay-out of floss are manifold, including the ability to provide a number of desirable optional features in a vial floss dispenser. Many of these are illustrated in FIGS. 1, 4, and 5. It is important in any floss dispenser to provide a user with a blade 50 (i.e., some mechanism with which to cut the floss for use). While this mechanism may comprise any suitable cutting device, the conventional cutting blade 50 illustrated is preferred. This blade 50 comprises a clip 52, which slides into a pre-cut slot 54 in the cap 30, and a raised cutting edge 56 around which floss 22 is severed. In the preferred embodiment of the present invention shown, the cutting blade 50 is oriented on the opposite side of the cap 30 from the opening 48. This spaced apart relationship provides an exposed segment 58 (or "leader") of floss that can be grasped by the user.

To further assist a user in grasping the floss, the top of the cap also includes an indent 60 between the opening 48 and the blade 50. This indent 60 amply exposes the floss segment 58 above the top of the cap and allows a user to easily clasp around the floss.

One of the chief advantages of the floss dispenser of the present invention is that floss need not be left unprotected on the side of the floss container. With the floss exiting the container in the cap itself, the entire top surface of the dispenser may then be covered with a lid 62. Such a lid may be: completely removable and disposable after purchase; completely removable and re-sealable between uses; or permanently attached to the dispenser, such as with a lanyard or hinge mechanism, to assure that the floss container can be repeatedly re-sealed between uses without risk of loss of the cap.

Shown in FIGS. 1 through 4 is the preferred lid 62 device for use with the present invention. This lid 62 is connected to the cap 30 with hinge 64. The lid 62 completely seals over the entire top surface 34 of the cap 30 between uses, thoroughly sealing the opening 48, the exposed floss segment 58, and the blade 56. This not only protects against contamination of the floss segment 58, but also reduces risk of accidental injury caused by the blade 56. Finally, a thumb tab 66 is provided to on the lid to assist in opening.

While the preferred floss container of the present invention has been illustrated and described in this application, its should be appreciated that modifications and additions may be readily made within the basic concepts of the present invention. For example, the container 12 itself is preferably a cylindrical shape to minimize wasted container space, but the present invention may be modified to provide rectangular, hexagonal, or other cross-sectional shapes. Other possible modifications may include: providing a second disc on the upper end of the floss spool, perhaps allowing the spool to be inserted in either direction into the container; providing multiple openings within the cap for insertion of floss there through; providing different cutting mechanisms; providing a view window on the side of the vial container; etc.

As has been noted, the floss dispenser 10 of the present invention is a marked improvement over all previous vial-type floss containers. While certainly not limited to such use, the floss dispenser of the present invention is particularly suited for holding larger quantities of floss, such as spools containing 100 to 200 yards or more of floss.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A floss dispenser that comprises an essentially cylindrical vial case, the case including two ends and a longitudinal length and having an opening in at least one end;

a spool having floss wrapped around a hub, the spool rotatably disposed in the case and proportioned to be inserted into the case through the opening in its end with the hub of the spool mounted parallel to the length of the cylindrical case;

wherein the spool further includes a disc on one end of the hub, the disc assisting in centering the spool in the case while the spool is rotated within the case around a longitudinal axis of the hub, and a projection on the opposite end of the hub;

a cap removably mounted over the opening and sealing the opening in the end of the cylindrical case, the cap including a recess therein surrounded by a circular lip, the recess and lip receiving and centering the projection of the hub when the cap is sealing the opening in the case, and the cap further including at least one opening therein through which floss is threaded out of the end of the case, the opening in the cap being oriented outside of the lip in a groove between the lip and the case when the cap is mounted in place;

wherein when the spool is inserted within the case and the opening in the end of the case is sealed with the cap, the hub of the spool is retained within the recess in the cap and the spool spins easily within the case, with the floss paying-off freely through the opening in the cap.

2. The floss dispenser of claim 1 wherein a removable lid is provided on the cap to seal the opening in the cap.

3. The floss dispenser of claim 2 wherein the cap also includes a cutting blade;

wherein the lid seals the opening in the cap and the cutting blade when the floss dispenser is not in use.

4. The floss dispenser of claim 3 wherein the lid is further attached to the cap by a hinge.

5. The floss dispenser of claim 1 wherein the end of the case opposite the opening is sealed with a transparent plug; and the circular disc comprises transparent material;

wherein the transparent plug and the transparent disc provide a view of the amount of floss contained on the hub.

6. The floss dispenser of claim 1 wherein said lip includes a portion that is tapered inwardly toward the recess so as to assist in mounting the recess over the projection of the hub.

7. The floss dispenser of claim 1 wherein a cutting blade is mounted in a top surface of the cap; and an indent is provided in the top surface of the cap between the opening and the cutting blade, whereby the floss exiting the case via the opening in the cap and held in place within the cutting blade can be readily grasped by a user.

8. The floss dispenser of claim 7 wherein a lid is attached to the cap by a hinge and further mounted over the cap when the dispenser is not in use so as to cover the opening in the cap, the cutting blade, and floss held between the opening and the cutting blade.

* * * * *